United States Patent [19]

Varterasian et al.

[11] Patent Number: 4,653,327
[45] Date of Patent: Mar. 31, 1987

[54] ACOUSTICAL INSPECTION METHOD FOR INSPECTING THE CERAMIC COATING OF CATALYTIC CONVERTER MONOLITH SUBSTRATES

[75] Inventors: John H. Varterasian, Livonia; Dwight A. Blaser, Fraser, both of Mich.

[73] Assignee: General Motors Corporation, Detroit, Mich.

[21] Appl. No.: 863,146

[22] Filed: May 14, 1986

Related U.S. Application Data

[63] Continuation-in-part of Ser. No. 850,042, Apr. 10, 1986.

[51] Int. Cl.⁴ .............................................. G01N 29/60
[52] U.S. Cl. ....................................... 73/579; 73/118.1; 73/596; 181/0.5
[58] Field of Search ...................... 73/118.1, 579, 582, 73/596; 181/0.5

[56] References Cited

U.S. PATENT DOCUMENTS 4,480,473 11/1984 Varterasian ............................ 73/596

Primary Examiner—Howard A. Birmiel
Attorney, Agent, or Firm—R. L. Phillips

[57] ABSTRACT

An acoustic inspection method is disclosed for determining in a catalytic converter monolith substrate whether a ceramic coating was applied in a predetermined amount and uniformly to the surface of exhaust gas passages extending therethrough and whether the ceramic coating is blocking any of the passages. The method includes mounting the substrate in an acoustically sealed structure so as to form a throat communicating a speaker at an entrance end of the coated passages with an empty resonator cavity at an exit end of the coated passages and thereby form a Helmholtz resonator. The speaker is then driven to produce a continuous sound wave through the coated passages into the resonator cavity at a predetermined frequency approximately the natural frequency of the resonator to thereby produce oscillatory sound waves through the coated passages at the same frequency. The substrate is then reversely mounted and the previous step is repeated. The phase angles of the sound waves at the entrance and exit ends of the coated substrate passages are then compared with respect to those of a reference sound wave of the same frequency passed in like manner through a reference substrate known to have the desired quantity and uniformity of coating on the passages and no blockage. Whether or not the passages of the substrate being inspected have the prescribed quantity and uniformity of coating and any blockage is then detected on the basis of the occurrence of a prescribed difference in the phase angles.

6 Claims, 5 Drawing Figures

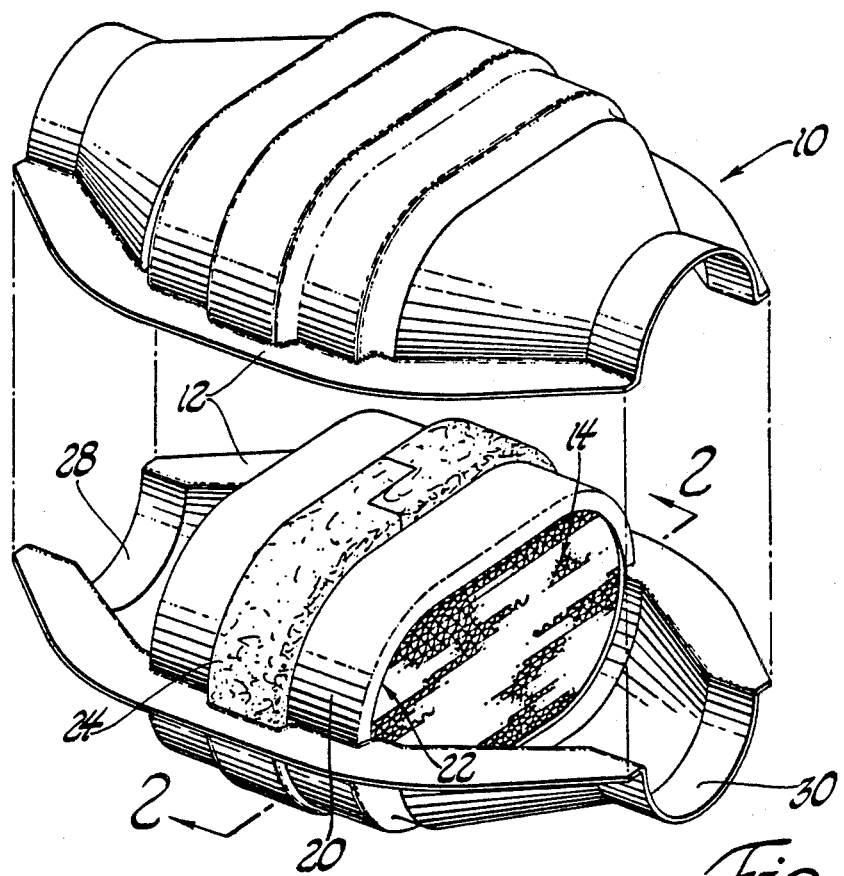
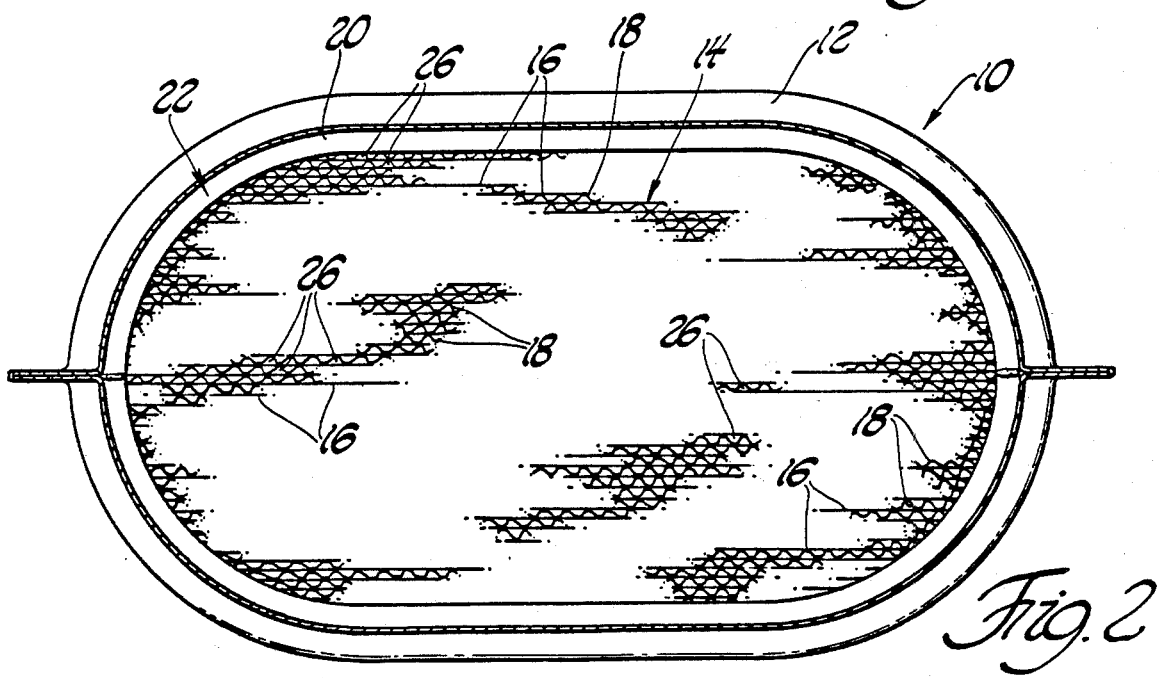

PHASE ANGLE BETWEEN SQUARE WAVES—DEGREES

ACOUSTICAL INSPECTION METHOD FOR INSPECTING THE CERAMIC COATING OF CATALYTIC CONVERTER MONOLITH SUBSTRATES

This is a continuation-in-part application of U.S. Ser. No. 850,042, filed Apr. 10, 1986.

TECHNICAL FIELD

This invention relates to methods of inspecting the ceramic coating of catalytic converter monolith substrates and more particularly to an acoustical method for inspecting the amount of coating, the uniformity of the coating and whether there is blockage by the coating.

BACKGROUND OF THE INVENTION

In the manufacture of catalytic converter monoliths, the monolith substrate is normally formed of extruded ceramic material or stacked corrugated metal foil so as to have many passages extending therethrough for exhaust gas flow past a catalyst deposited on the passages walls. The many passages form a large surface area within a small cross-sectional envelope that is normally further minimized significantly for both space and material savings by treating the surface with a ceramic wash coat such as alumina so as to form a coating thereon of greatly expanded surface area to serve as the actual base for the noble metal catalytic material. However, the normal amount of washcoat then reduces the flow area significantly (e.g. by as much as 25%). And thus, it will be appreciated that an excess of washcoat could unnecessarily increase the engine back pressure significantly, while insufficient washcoat could significantly reduce the long term effectiveness of the catalytic action.

In the manufacturing process, the object then is to apply the correct or proper amount of ceramic coating to the monolith substrate passages; i.e. an amount that allows proper catalytic action without unduly increasing the engine back pressure. The proper amount to apply can be precisely determined but the problem is in the accurate application which to date by all methods known can result in a significant number of out of tolerance substrates. For example, there may be too much or too little coating, the passages may be tapered because of nonuniform coating caused by "sagging" or "running" of the coating prior to drying, and/or the coating may have plugged some of the passages. Since the performance of the converter is highly dependent on the proper amount and distribution of the washcoat, it is necessary to determine whether the desired amount of coating was applied, whether it was applied uniformly along the passages, and whether any passages were blocked. Moreover, it is desirable that the inspection be made rapidly without loss of accuracy that there be 100% inspection available and that the method be nondestructive of the monolith substrates as well as not require their special clean up. The present methods typically involve computation based on coating weight, and measurements by pressure drop and radiogauging and as a result are deficient in various respects.

SUMMARY OF THE INVENTION

The method according to the present invention provides for acoustically inspecting such ceramic coated monolith substrates both rapidly and accurately at the completion of their coating by applying the principles of a Helmholtz resonator to measure the flow area of a coated monolith substrate and from this infer whether the coating was applied properly. The present invention recognizes and utilizes the fact that the acoustic natural frequency of a Helmholtz resonator is a function of the resonator's physical dimensions as well as several constants and that by employing the coated monolith substrate as the throat to form such a resonator, a simple acoustical inspection method may then be applied preferably using a speaker, two microphones, and a sound wave phase angle processor to infer the flow area of the coated monolith substrate operating as such and thereby whether the coating was applied properly thereto.

In the inspection apparatus, there is provided an acoustically sealed structure with the speaker at one end, an empty resonator cavity at an opposite end and a connecting passage therebetween in which is mounted the coated monolith substrate that is to be inspected. The speaker is driven to produce a continuous low frequency sound wave through the coated passages into the resonator cavity. This apparatus forms in effect a Helmholtz resonator that responds similarly to a spring-mass-damper system and has a resonant or natural frequency at which large oscillatory air motions will occur through the coated monolith substrate. With the coated monolith substrate used as the throat, the natural frequency, $f_n$, of the acoustic system is directly related to the existing flow area of the coated passages according to the equation $$f_n = c/2\pi \sqrt{A_m/VL_m} \tag{1}$$

where
c = speed of sound,
$A_m$ = total area of monolith substrate passages,
$L_m$ = effective length of monolith substrate, and
V = volume of resonator cavity.

And since the length of each coated monolith substrate, the volume of the resonator cavity, and the speed of sound all remain fixed, the natural frequency is as a result proportional to the square root of the flow area of the monolith substrate; i.e., $$f_n \alpha \sqrt{A_m} . \tag{2}$$

And thus the flow area can be determined by varying the excitation frequency to the speaker until peak sound pressure occurs in the cavity as monitored by the one microphone therein with the coated monolith substrate incorporated as the throat of this thus formed Helmholtz resonator. The flow area thus determined can then be used to infer the amount of coating by the known effect its thickness has on the flow area.

But moreover, the natural frequency can also be identified by measuring the phase angle between the signals of the two microphones located at the opposite ends of the substrate and from this and with reference to a substrate known to be properly coated, an even greater range and degree of inspection may be made and in a manner well suited for fully automatic on-line inspection in production. In this, the most preferred method, the two microphones are used to monitor the acoustic pressure at both ends of the coated monolith substrate, and the resulting signals are processed to determine phase angle information to infer the actual area of the substrate.

Furthermore, with phase angle comparison it has been found that the uniformity of the coating can be determined by simply reversing the mounting of the substrate and repeating the phase angle inspection step as will be further disclosed later. In addition, a go and no-go type of inspection is implemented with the phase angle signals and processor to enable inspection within a very short time (e.g. a few seconds) and to a very fine degree ( e.g. detecting flow area deviations as small as 1%). In such inspection, improper coating is detected by the occurrence of a certain difference in phase angle from a fixed reference so as to not require human operator judgment so that with automation the method of the present invention can be used in an unattended factory for 100% on-line inspection in production.

DESCRIPTION OF PREFERRED EMBODIMENT

These and other objects, advantages and features of the present invention will become more apparent from the following description drawings in which:

FIG. 1 is an exploded view of a catalytic converter having a monolith whose substrate has a ceramic coating to which the acoustical method of the present invention is adapted to inspect.

FIG. 2 is a cross-sectional view taken along the line 2—2 in FIG. 1.

Figure 3:
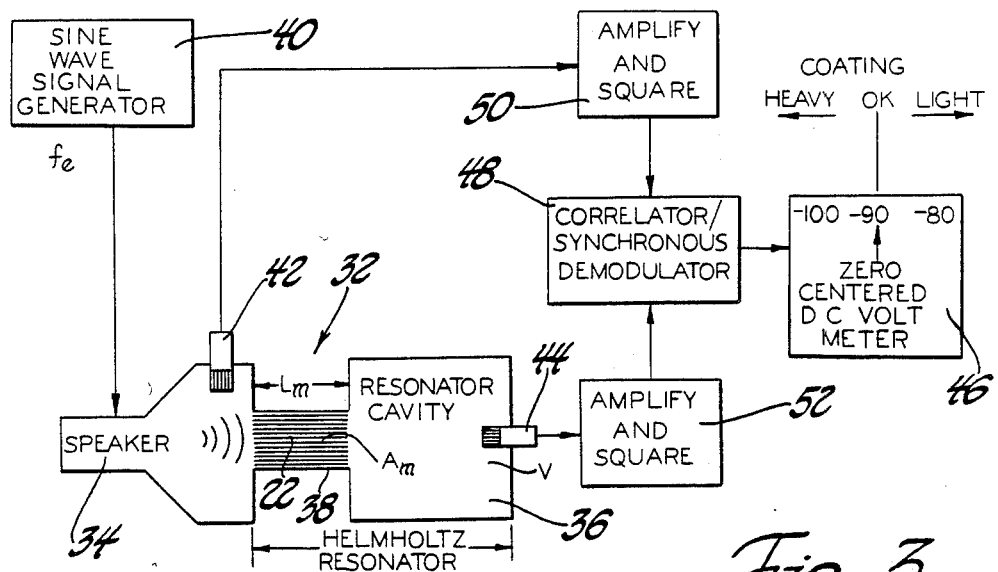
FIG. 3 is a block diagram of apparatus for implementing the acoustical method of the present invention to inspect the coated monolith substrate in FIG. 1.

Referring to the drawings, wherein like reference numbers designate like or corresponding parts throughout the several views, there is shown in FIGS. 1 and 2 a catalytic converter 10 of the monolith type used in a motor vehicle to eliminate the undesirable constituents in internal combustion engine exhaust gases. The converter shown is like that disclosed in U.S. Pat. No. 4,559,205 issued Dec. 17, 1985 and assigned to the assignee of this invention and hereby incorporated by reference. Relating those parts believed particularly helpful to understanding the present invention, the converter includes a two-piece sheet metal housing 12 enclosing a monolith 14 formed of a metal substrate coated with a ceramic washcoat of alumina and then a suitable catalyst. The metal substrate is formed of plain and corrugated metal foil sheets 16 and 18 that are retained together by a two-piece sheet metal canister 20 as a subassembly 22 for application of the ceramic coating and catalyst and mounting in the converter housing. An annular seal 24 formed of intumescent material provides sealing between the exterior of the canister and the interior of the housing and the monolith forming sheets are arranged and configured so as to define many passages 26 of thus extensive catalyst treated surface area connecting the converter's inlet 28 and outlet 30. However, it will also be understood that the acoustical inspection method of the present invention while disclosed inspecting the above metal monolith substrate is also applicable, as will become readily apparent, to inspecting other forms of monolith substrates such as an extruded ceramic one where a ceramic washcoat is similarly applied for surface area gain.

Apparatus for acoustically inspecting such monolith substrates as to the amount and uniformity of the ceramic washcoat or the like applied thereto and as to whether there is blockage of some of the passages therein by such coating is shown in FIG. 3. The apparatus comprises an acoustically sealed structure 32 with a speaker 34 at one end, an empty cavity or resonator chamber 36 at an opposite end, and a connecting throat section 38 in the center that is adapted to have the coated monolith substrates to be inspected readily mounted therein one at a time. A conventional sine wave generator 40 is operated to drive the speaker to produce a continuous low frequency ( e.g. less than 165 Hz) acoustic wave that travels through the passages of the substrate into the resonator chamber. This forms a Helmholtz resonator, as noted in FIG. 3, that responds similarly to a spring-mass-damper system and has a resonant or natural frequency at which large oscillary air motions will occur through the coated monolith substrate being inspected. These motions are monitored by two microphones 42 and 44 that are located in the sealed structure at the face of the speaker and in the resonator cavity, respectively, so as to sense the acoustic pressure at both ends (entrance and exit) of the coated monolith substrate. The resulting signals are processed to determine phase angle information that is used to infer the flow area and from that whether the coating was applied properly as will now be described in detail with reference to the most preferred manner.

The acoustical method of the present invention is based, as indicated earlier, on the fact that the acoustic natural frequency of a Helmholtz resonator is a function of the resonator's physical dimensions $A_m$, $L_m$ and V (see FIG. 3) and that by making the coated monolith substrate the throat of such a resonator, the natural frequency, $f_n$, is thus made directly related to the substrate's flow area according to the afore-presented Equation (1) and in particular is thus made proportional to the square root thereof according to the afore-presented Equation (2). As a result, the flow area can be determined by varying the excitation frequency to the speaker until peak sound pressure occurs in the resonator cavity with the coated monolith substrate serving as the throat. And from this determination of the flow area, the amount of ceramic coating can also be inferred as will be demonstrated with respect to the most preferred method utilizing measurement of the phase angle and the added advantages thereof.

The natural frequency of the thus structured Helmholtz resonator incorporating a coated monolith substrate as the throat can also be identified by measuring the phase angle between the signals of the two microphones at the entrance and exit of the coated substrate passages. For instance, at the resonant or natural frequency, the phase angle of the signal from the output microphone 44 is −90° out-of-phase (phase lag) with the signal from the input microphone 42. This is shown by the curve (a) in FIG. 4 where the phase angle is plotted as a function of frequency using a properly coated or "reference" monolith substrate as the resonator throat element.

In addition to a −90° phase angle at the natural frequency, the phase response curve has a finite and maximum slope at $f_n$. This slope is a function of the acoustic damping that results because of the radiation of sound into the regions surrounding the coated monolith substrate and viscous losses associated with the movement of fluid (air) through the narrow passages of the substrate. And it is the slope at the natural frequency that determines the maximum sensitivity or gain of the above inspection system; i.e. change of phase angle per unit change of flow area. With smaller passages, the acoustical damping increases while the absolute value of the slope (gain) decreases. Alternatively, with larger passages, the opposite occurs. However, it will also be appreciated that very high gain or sensitivity also occurs with very little damping but this is to be avoided because of the nonlinear or erratic output that could result.

Figure 4:
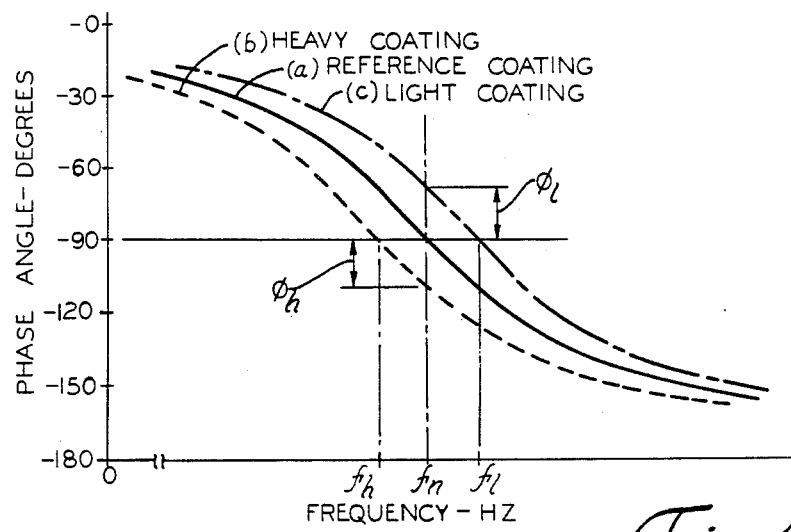
FIG. 4 is a graph of phase angle as a function of frequency from signals from the microphones in the apparatus in FIG. 3 obtained from inspecting a coated monolith substrate with the proper coating and also one with a heavy coating and one with a light coating.

Using the apparatus in FIG. 3 and with the Helmholtz resonator phase angle characteristics corresponding to a reference coated monolith substrate shown by the curve (a) in FIG. 4, flow area inspection with maximum sensitivity is obtained as follows. First, the speaker excitation frequency, $f_e$, is adjusted or tuned, to produce a $-90°$ phase angle (i.e. $f_e = f_n$) with a properly coated or reference monolith substrate operating as the resonator throat. This frequency is then held while other substrates following their coating in the manufacturing process and prior to final assembly are succeedingly substituted for the reference coated substrate as the resonator throat. The phase angles resulting from these succeeding units are then used as a measure of the flow area of those units relative to the reference unit. This is shown in FIG. 4 by phase angle characteristics found for monolith substrates with less flow area and thus a heavy or thick coating indicated by curve (b) and those with more flow area and thus a light or thin coating indicated by curve (c). Viewing these curves, it is seen that the curves (b) and (c) are substantially identical to the reference curve (a) but are shifted to the left and right thereof, respectively. In the case of curve (b), the shift occurred because the heavier coating reduced the flow area which, in turn, lowered the resulting natural frequency, $f_h$, of the Helmholtz resonator then in effect in compliance with Equation (2). Therefore, with an initial excitation frequency of $f_e = f_n$, the phase angle resulting from a heavily coated monolith is $-(90° + \phi_h)$ as shown. On the other hand, for a monolith substrate with light coating, the resulting natural frequency, $f_l$, is greater than $f_n$, and the corresponding phase angle is $-(90° - \phi_l)$.

In practice in general, the phase angles $\phi_h$ and $\phi_l$ will correspond to the normal extremes of washcoat thickness variations and may, for example, both be about 10°. Therefore, all other coated monolith substrates in this group will, produce phase angles within the band $-90° \pm 10°$. However, properly coated monoliths will produce phase angles within a smaller tolerance band like $-90° \pm$, for instance. Therefore, any substrate within this group that produces a phase angle outside of the ≡ band is inferred as having either too heavy or too light a coating and is unacceptable as being out of the prescribed tolerance. As a result, a phase meter that is calibrated with $-90°$ at the center, and $-100°$ and $-80°$, respectively, at the left and right ends can be used to measure and inspect whether the proper coating has been applied. This phase meter may be simply a zero centered DC volt meter 46 as shown in FIG. 3 that receives the output of a correlator/synchronous demodulator 48 to which the sine wave signals from the microphones 42 and 44 are delivered by amplifying and squaring circuits 50 and 52 as described in greater detail later. After the system is calibrated by inserting a reference substrate and adjusting $f_e = f_n$, a phase angle of $-90°$ ($\pm 3°$ tolerance for instance) resulting from a substrate under inspection indicates that the proper amount of washcoat was applied, or that only minimal blockage of the passages by the coating exists. On the other hand, a phase angle whose absolute value is out of the tolerance band indicates an improper amount of coating, or too much blockage. Moreover, the phase angle as monitored by the phase meter, in addition to determining whether the coating is unacceptable, also indicates to which extent it is, i.e. either too heavy or too light a coating.

Inspection of the washcoat thickness for uniformity along the length of the substrate passages is obtained by inspecting the flow area in both directions. This results from the discovery that the indicated phase angles will be different if there is nonuniformity in coating thickness depending on the direction the substrate is oriented in the resonator during the inspection. This is because the indicated phase angle was found to be more sensitive to the entrance flow area near the speaker than it is to the exit flow area near the resonator cavity. That is, when the end of a substrate with a slightly lower flow area, such as results from sagging or running of the coating prior to drying, is adjacent the speaker, the absolute value of indicated phase angle is greater than when the unit is reversed or turned around. Accordingly, when the same phase angle is observed for both directions, it can be inferred that the substrate is uniformly coated. On the other hand, when these phase angles differ, it can be inferred that the coating is nonuniform or tapered along the length of the substrate.

The most preferred phase angle readout for the acoustic inspection method is obtained through the signal processing stages in FIG. 3. In this regard, the acoustic activity at each end of the Helmholtz resonator is monitored by the two microphones 42 and 44 whose sine waves are amplified and squared by the respective circuits 50 and 52 of conventional layout. This operation preserves the phase relationship of the sine waves and results in square waves with fixed amplitudes. That is, regardless of the amplitudes of the acoustic pressure signals, the amplitudes of the square waves will remain fixed. As a result, the system is essentially insensitive to amplitude changes that might occur due to temperature changes, aging, and other "noise" inputs, and responds only to the relevant phase variations that result from different flow areas.

Figure 5:
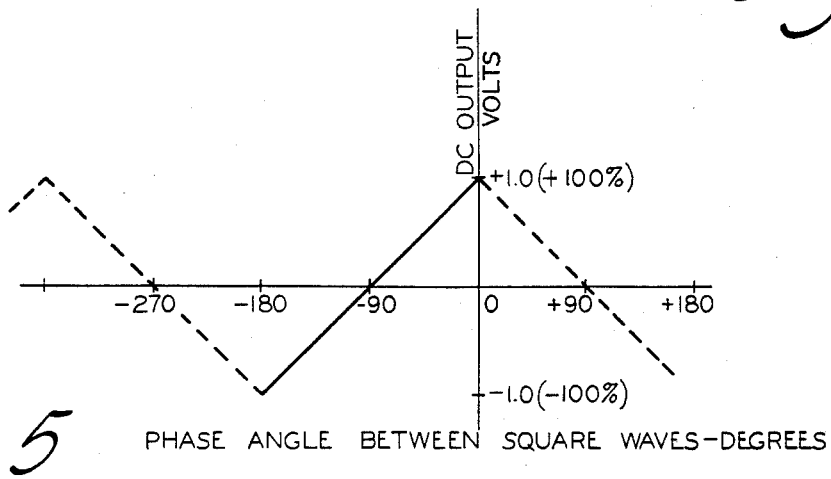
FIG. 5 is a graph of the DC output voltage as a function of phase angle for the correlator/synchronous demodulator in the apparatus in FIG. 3.

The square waves are input to the correlator/synchronous demodulator 48 which is a unit like the arrangement for a similar processing purpose disclosed in my U.S. Pat. No. 4,480,473 (see FIG. 6) issued Nov. 6, 1984 and hereby incorporated by reference. As shown in FIG. 5, the output of this stage is a DC analog voltage that varies linearly (within 180° bands) with the phase angle difference between the square waves. That is, when the signals are in-phase, $\phi = 0°$ (+100% positive correlation), the DC voltage is at its maximum positive value( +1 volt for instance). As $\phi$ decreases, the voltage decreases as shown by the solid line in FIG. 5. At $\phi = -90°$ (no correlation), the correlator output is 0 volts. Then as $\phi$ approaches $-180°$ ($-100\%$ negative correlation), the output is $-1$ volt. As can be seen, a linear relationship exists between and DC voltage in the range where $-180°$ that on both sides of this range, the function repeats itself as shown by the dashed portion thereof.

Only the solid portion of the curve in FIG. 5 is relevant to the inspection. As such, when the DC voltage from the correlator 48 inputs to the zero-centered DC voltmeter 46, this instrument functions as a phase meter in practicing the inspection method. That is, the center of the meter indicates $-90°$, whereas, the left and right ends indicate angles that are proportional to the heaviest and the lightest expected coatings; for instance, $-100°$ and $-80°$ as shown in FIG. 3 for the case where $\phi_h = \phi_l = 10°$ as earlier related. These end points are determined experimentally for each different type of monolith which may have either a metal or ceramic substrate and should be in the linear range, i.e. the solid line in FIG. 5. And thus the meter system in conjunction with the Helmholtz resonator with a coated monolith substrate specimen as the throat results in an acoustic phase angle measurement proportional to the flow area of this substrate specimen and therefore a measure of the amount of coating thereon.

The above inspection method can fundamentally operate at any excitation frequency, but it is preferred that the system be calibrated by tuning such frequency to the resonant frequency of the Helmholtz resonator for at least two reasons. First, it results in very nearly maximum sensitivity to flow blockage when $\phi_h$ and $\phi_l$ are nearly equal. That is, the greatest difference between curves (b) and (c) in FIG. 4 occurs in the frequency range near $f_n$. Secondly, $f_n$ is a well defined frequency, producing a $-90°$ phase angle with a reference or properly coated substrate, that makes calibration easy and consistent.

On the other hand, if circumstances should change in the manufacturing process such that $\phi_h$ and $\phi_l$ were not similar in magnitude, then the initial tuning strategy could be revised to maintain a high sensitivity. For example, if lighter than normal coatings were no longer a possibility in the manufacturing process, then the initial excitation or tuning frequency could be offset to a value less than $f_n$. More specifically, in such a case, the maximum sensitivity is obtained with the excitation frequency equal to the geometric mean of $f_n$ and $f_h$, as given by the equation, $$f_e = \sqrt{f_n f_h} \quad (3)$$

This criterion ensures that the difference between the two phase responses is maximized for the inspection of the coated substrates. It assumes, however, that the acoustic damping (i.e. slope of the curve) for both substrates is the same, which is usually a good approximation. Similarly, if only substrates with lighter coating are of concern (i.e. heavy coatings are not a possibility because of the manufacturing process), the tuning or excitation frequency for maximum sensitivity is equal to the geometric mean of $f_n$ and $f_l$, as given by, $$f_e = \sqrt{f_n f_l} \quad (4)$$

And again, the small changes in substrate acoustic damping are considered negligible.

The sensitivity or gain of the system will be defined as the phase angle change for a 1% change in the flow area and depends primarily on the slope of the phase angle response curve at the natural frequency. Accordingly, the sensitivity is a function of the physical dimensions and configuration of the substrate and theoretically would be different for each substrate shape and passage geometry. Considering the sensitivity of the system to the oval substrate shown and recalling that the Helmholtz resonator is analogous to a second order mechanical system and thus can be modeled as a mass, spring and damper, the phase angle angle response curves therefore can be described with the expression used for the phase angle between displacement and force in a mechanical system. This is given by, $$\phi = -\tan^{-1}\left\{ \frac{2\zeta(f_e)/(f_n)}{[1-(f_e/f_n)^2]} \right\}. \quad (5)$$

In Equation (5), $f_e$ is the excitation frequency, $f_n$ is the system's natural frequency, and $\zeta$ is the acoustic damping factor. And it will be noted that $\zeta$ can be determined from the phase angle response curve using the relationship, $$\zeta = \frac{180}{\pi f_n \frac{(\Delta\phi)}{\Delta f}} \quad (6)$$

where $\Delta\phi \cdot \Delta f$ is the slope of the response curve at the natural frequency. For example, it was noted for a certain reference substrate having a normal and uniform coating that $$f_n = 140.6 \text{ Hz}, \quad (7)$$

and $$\Delta\phi/\Delta f = 2.085°/\text{Hz}, \quad (8)$$

therefore, $$\zeta = 0.195. \quad (9)$$

With this parameter it is possible to calculate the phase angle of the inspection system with a test substrate with a flow area different from that of the reference substrate, and, therefore, to determine the sensitivity of the inspection system. This calculation is based on the condition that the excitation frequency, $f_e$, is initially tuned to be equal to $f_r$, the natural frequency corresponding to the reference substrate. Accordingly, from Equation (5), $$\phi_t = -\tan^{-1}\left\{ \frac{2\zeta(f_r/f_t)}{[1-(f_r/f_t)^2]} \right\}. \quad (10)$$

where $f_t$ is the natural frequency corresponding to the test substrate. Then from Equation (2), $$f_r/f_t = \sqrt{A_r/A_t} = \sqrt{R} \quad (11)$$

where $A_r$ is the flow area corresponding to the reference substrate, $A_t$ is the flow area of the test substrate, and R is the ratio of the flow areas and is equal to $A_t/A_r$. By substituting Equation (11) into (10), $$\phi_t = [-\tan^{-1} 2\zeta \sqrt{R} /(R - 1)]. \tag{12}$$

As a result, Equation (12) describes the phase angle of any test substrate in the inspection system in terms of the ratio of the flow areas. For instance, in the above example an increase of 1% in flow area (R 32 1.01) would result in a phase angle of $-88.5°$, or a change in phase angle of 1.5°. Therefore, the sensitivity for a uniform change of flow area is 1.5°/1%. However, the sensitivity for a nonuniform change of area that results when only a few passages are blocked has been found to be nearly half of the uniform value. In addition, the sensitivity for a discrete blockage was found to depend somewhat on the actual location of the blockage. Moreover, Equation (12) can be used to show that the inspection system's phase angle limits such as those above given as $-80°$ and $-100°$ correspond to an area increase of 7.1% and a decrease of 6.6%, respectively.

In the description thus far, it has been assumed that the speed of sound is the same during each inspection. However, the speed of sound does vary with temperature and this will therefore affect the relationship between the acoustic phase angle and the flow area of the substrate. Addressing this situation, the speed of sound in air varies as the square root of the absolute temperature as given by, $$c = c_o \sqrt{1 + T/273} \tag{13}$$

where $c_o$ = speed of sound at 0° C.

= 331.1 m/s and T=temperature, °C. Hence, from Equation (1), the natural frequency of the Helmholtz resonator and the resulting phase angles used in the present method also vary with temperature. Accordingly, for consistent inspection results, the system needs to be recalibrated to compensate for any substantial temperature change as will now be demonstrated.

By substituting Equation (13) into Equation (1), the natural frequency of a Helmholtz resonator at a temperature T is given by, $$f_n = c_o/2\pi \sqrt{(1 + T/273)(A_m/VL_m)} . \tag{14}$$

Therefore, a ratio of the natural frequencies for air temperatures $T_1$ and $T_2$ is given by, $$f_1/f_2 = \sqrt{(273 + T_1)/(273 + T_2)} . \tag{15}$$

In Equation (15), $f_1$ corresponds to the natural frequency of a coated substrate at temperature $T_1$, whereas $f_2$ corresponds to the natural frequency of the same substrate at temperature $T_2$. For instance, for a reference substrate having an oval cross-section as shown and for which the natural frequency was found to be 138.9 Hz at a temperature of 22° C., the resulting natural frequency at any other temperature, T, is given by, $$f_n = 8.1 \sqrt{273 + T} , \tag{16}$$

and the natural frequency sensitivity to temperature is $$\Delta f_n/\Delta T = 0.235 \text{ Hz/°C}. \tag{17}$$

On comparing measured values of natural frequency versus temperature for this reference substrate with the theoretical, it was found that there was good actual correlation therebetween.

With such correlation found, the phase angle as a function of temperature for this reference substrate is then obtained by substituting Equation (15) into (5) with the reference damping factor $\zeta = 0.195$. As a result, $$\phi = -\tan^{-1}[6.7 \sqrt{(273 + T)/(T - 22)} , \tag{18}$$

and the phase angle sensitivity to temperature given by the derivative is, $$\Delta\phi/\Delta T = 0.498 \text{ °/°C}. \tag{19}$$

Thus the combined effects of excitation frequency and temperature on phase angle can be predicted and compensated for accordingly. For instance, when the above described system was initially calibrated with $\phi = -90°$ using a substrate with a normal and uniform coating as the reference, the excitation frequency was 138.9 Hz with the temperature at 22° C. However, if the temperature had increased for example to 25° C., the resulting phase angle would have changed to $-88.5°$ according to Equation (19). As a result, for consistent inspection results, it would be necessary to recalibrate the system by increasing the excitation frequency to 139.6 Hz where the phase angle is again $-90°$. Also, it will be understood that the temperature of the reference substrate should be representative of the temperature of the substrates being inspected.

The above described embodiment is illustrative of the invention which may be modified within the scope of the appended claims.

The embodiments of the invention in which an exclusive property or privilege is claimed are defined as follows:

1. An acoustic inspection method for determining in a catalytic converter monolith substrate whether a ceramic coating was applied in a predetermined amount to the surface of exhaust gas passages extending therethrough and whether the ceramic coating is blocking any of the passages, comprising the steps of:
  (a) mounting a catalytic converter monolith substrate with ceramic coated exhaust gas passages extending therethrough in an acoustically sealed structure so as to form a throat communicating a speaker at an entrance end of the coated passages with an empty resonator cavity at an exit end of the coated passages and thereby form a Helmholtz resonator,
  (b) driving the speaker to produce a continuous sound wave through the coated passages into the resonator cavity at a predetermined frequency and thereby produce oscillatory sound waves through the coated passages at the same frequency,
  (c) comparing the phase angles of the sound waves at the entrance and exit ends of the coated substrate passages and with respect to those of a reference sound wave of the same frequency passed in like manner through a reference substrate known to have the desired quantity of coating on the passages and no blockage, and (d) detecting whether or not the passages of the substrate being inspected have the prescribed quantity and any blockage on the basis that the occurrence of a prescribed difference in the phase angles infers a deviation in the total flow area of the passages and thereby a deviation from the desired coating as to amount and lack of blockage.

2. An acoustic inspection method for determining in a catalytic converter monolith substrate whether a ceramic coating was applied in a predetermined amount to the surface of exhaust gas passages extending therethrough and whether the ceramic coating is blocking any of the passages, comprising the steps of:

(a) mounting a catalytic converter monolith substrate with ceramic coated exhaust gas passages extending therethrough in an acoustically sealed structure so as to form a throat communicating a speaker at an entrance end of the coated passages with an empty resonator cavity at an exit end of the coated passages and thereby form a Helmholtz resonator, (b) driving the speaker to produce a continuous sound wave through the coated passages into the resonator cavity at a predetermined frequency approximately the natural frequency of the resonator and thereby produce oscillatory sound waves through the coated passages at the same frequency, (c) comparing the phase angles of the sound waves at the entrance and exit ends of the coated substrate passages and with respect to those of a reference sound wave of the same frequency passed in like manner through a reference substrate known to have the desired quantity of coating on the passages and no blockage, and (d) detecting whether or not the passages of the substrate being inspected have the prescribed quantity and any blockage on the basis that the occurrence of a prescribed difference in the phase angles infers a deviation in the total flow area of the passages and thereby a deviation from the desired coating as to amount and lack of blockage.

3. An acoustic inspection method for determining in a catalytic converter monolith substrate whether a ceramic coating was applied uniformly to the surface of exhaust gas passages extending therethrough, comprising the steps of:

(a) mounting a catalytic converter monolith substrate with ceramic coated exhaust gas passages extending therethrough in an acoustically sealed structure so as to form a throat communicating a speaker at an entrance end of the coated passages with an empty resonator cavity at an exit end of the coated passages and thereby form a Helmholtz resonator, (b) driving the speaker to produce a continuous sound wave through the coated passages into the resonator cavity at a predetermined frequency and thereby produce oscillatory sound waves through the coated passages at the same frequency, (c) reversing the mounting of the substrate so that the entrance end is now near the resonator cavity and the exit end is now near the speaker and then repeating step (b), (d) comparing the phase angles of the sound waves at the entrance and exit ends of the coated substrate passages and with respect to those of a reference sound wave of the same frequency passed in like manner through a reference substrate known to have the desired quantity and uniformity of coating on the passages and no blockage, and (e) detecting whether or not the passages of the substrate being inspected have the prescribed uniformity of coating on the basis that a prescribed difference in the phase angles with reversal of the substrate mounting infers a deviation in the total flow areas at the entrance and exit ends and thereby a deviation from the desired coating as to uniformity along the length of the passages.

4. An acoustic inspection method for determining in a catalytic converter monolith substrate whether a ceramic coating was applied uniformly to the surface of exhaust gas passages extending therethrough, comprising the steps of:

(a) mounting a catalytic converter monolith substrate with ceramic coated exhaust gas passages extending therethrough in an acoustically sealed structure so as to form a throat communicating a speaker at an entrance end of the coated passages with an empty resonator cavity at an exit end of the coated passages and thereby form a Helmholtz resonator, (b) driving the speaker to produce a continuous sound wave through the coated passages into the resonator cavity at a predetermined frequency approximately the natural frequency of the resonator and thereby produce oscillatory sound waves through the coated passages at the same frequency, (c) reversing the mounting of the substrate so that the entrance end is now near the resonator cavity and the exit end is now near the speaker and then repeating step (b), (d) comparing the phase angles of the sound waves at the entrance and exit ends of the coated substrate passages and with respect to those of a reference sound wave of the same frequency passed in like manner through a reference substrate known to have the desired quantity and uniformity of coating on the passages and no blockage, and (e) detecting whether or not the passages of the substrate being inspected have the prescribed uniformity of coating on the basis that a prescribed difference in the phase angles with reversal of the substrate mounting infers a deviation in the total flow areas at the entrance and exit ends and thereby a deviation from the desired coating as to uniformity along the length of the passages.

5. An acoustic inspection method for determining in a catalytic converter monolith substrate whether a ceramic coating was applied in a predetermined amount and uniformly to the surface of exhaust gas passages extending therethrough and whether the ceramic coating is blocking any of the passages, comprising the steps of:

(a) mounting a catalytic converter monolithic substrate with ceramic coated exhaust gas passages extending therethrough in an acoustically sealed structure so as to form a throat communicating a speaker at an entrance end of the coated passages with an empty resonator cavity at an exit end of the coated passages and thereby form a Helmholtz resonator, (b) driving the speaker to produce a continuous sound wave through the coated passages into the resonator cavity at a predetermined frequency and thereby produce oscillatory sound waves through the coated passages at the same frequency, (c) reversing the mounting of the substrate so that the entrance end is now near the resonator cavity and the exit end is now near the speaker and then repeating step (b), (d) comparing the phase angles of the sound waves at the entrance and exit ends of the coated substrate passages and with respect to those of a reference sound wave of the same frequency passed in like manner through a reference substrate known to have the desired quantity and uniformity of coating on the passages and no blockage, and (e) detecting whether or not the passages of the substrate being inspected have the prescribed quantity and uniformity of coating and any blockage on the basis that the occurrence of a prescribed difference in the phase angles without reversal of the substrate mounting infers a deviation in the total flow area of the passages and thereby a deviation from the desired coating as to amount and lack of blockage and that a prescribed difference in the phase angles with reversal of the substrate mounting infers a deviation in the total flow areas at the entrance and exit ends and thereby a deviation from the desired coating as to uniformity along the length of the passages.

6. An acoustic inspection method for determining in a catalytic converter monolith substrate whether a ceramic coating was applied in a predetermined amount and uniformly to the surface of exhaust gas passages extending therethrough and whether the ceramic coating is blocking any of the passages, comprising the steps of:

(a) mounting a catalytic converter monolithic substrate with ceramic coated exhaust gas passages extending therethrough in an acoustically sealed structure so as to form a throat communicating a speaker at an entrance end of the coated passages with an empty resonator cavity at an exit end of the coated passages and thereby form a Helmholtz resonator, (b) driving the speaker to produce a continuous sound wave through the coated passages into the resonator cavity at a predetermined frequency approximately the natural frequency of the resonator and thereby produce oscillatory sound waves through the coated passages at the same frequency, (c) reversing the mounting of the substrate so that the entrance end is now near the resonator cavity and the exit end is now near the speaker and then repeating step (b), (d) comparing the phase angles of the sound waves at the entrance and exit ends of the coated substrate passages and with respect to those of a reference sound wave of the same frequency passed in like manner through a reference substrate known to have the desired quantity and uniformity of coating on the passages and no blockage, and (e) detecting whether or not the passages of the substrate being inspected have the prescribed quantity and uniformity of coating and any blockage on the basis that the occurrence of a prescribed difference in the phase angles without reversal of the substrate mounting infers a deviation in the total flow area of the passages and thereby a deviation from the desired coating as to amount and lack of blockage and that a prescribed difference in the phase angles with reversal of the substrate mounting infers a deviation in the total flow areas at the entrance and exit ends and thereby a deviation from the desired coating as to uniformity along the length of the passages.

* * * * *